United States Patent [19]

Marquis et al.

[11] Patent Number: 4,939,281

[45] Date of Patent: Jul. 3, 1990

[54] METHOD FOR RECOVERING SOLID MOLYBDENUM COMPOUNDS

[75] Inventors: Edward T. Marquis, Austin; John R. Sanderson, Leander; Kenneth P. Keating, Georgetown, all of Tex.

[73] Assignee: Texaco Chemical Co., White Plains, N.Y.

[21] Appl. No.: 368,009

[22] Filed: Jun. 19, 1989

[51] Int. Cl.$^5$ .............................................. C01G 39/00
[52] U.S. Cl. ................................. 549/529; 210/702; 210/912; 423/55
[58] Field of Search ........................ 423/53, 55, 297; 210/702, 912; 549/529, 541; 75/108, 121

[56] References Cited

U.S. PATENT DOCUMENTS

| | | | |
|---|---|---|---|
| 3,763,303 | 10/1973 | Khuri | 423/54 |
| 3,819,663 | 6/1974 | Levine | 423/53 |
| 3,931,044 | 1/1976 | Maurin | 549/529 |
| 4,315,896 | 2/1982 | Taylor | 423/53 |
| 4,317,801 | 3/1982 | Taylor et al. | 423/54 |
| 4,317,802 | 3/1982 | Dagna | 423/53 |
| 4,405,572 | 9/1983 | Moore | 423/55 |
| 4,455,283 | 6/1984 | Sweed | 423/53 |
| 4,485,074 | 11/1984 | Poenisch | 423/55 |
| 4,598,057 | 7/1986 | Isaacs | 423/53 |

Primary Examiner—Robert L. Stoll
Assistant Examiner—Steven J. Bos
Attorney, Agent, or Firm—Jack H. Park; Kenneth R. Priem; Carl G. Ries

[57] ABSTRACT

A process for substantially completely removing a minor amount of molybdenum dissolved in a substantially anhydrous organic solution, such as a heavy distillation fraction resulting from the removal of unreacted propylene, propylene oxide and tertiary butyl alcohol from an epoxidation reaction mixture:

wherein from about 1 to about 10 wt. % of an aqueous solution of sodium meta borate containing from about 1 to about 10 wt. % of dissolved sodium meta borate is added to an organic solution containing dissolved molybdenum catalyst in an amount sufficient to provide a molar excess of sodium meta borate, based on the gram atoms of dissolved molybdenum in said organic solution, to provide a mixture, wherein the mixture is maintained at a temperature ranging from about ambient temperature up to about 100° C. at a pressure of about 0 to about 1,000 psig. for about 0.5 to about 5 hours, sufficient to precipitate at least about 95 mol % of the soluble molybdenum from the mixture, and wherein the mixture is filtered to obtain a filtrate containing not more than about 100 ppm of molybdenum.

12 Claims, No Drawings

METHOD FOR RECOVERING SOLID MOLYBDENUM COMPOUNDS

BACKGROUND OF THE INVENTION

1. Field of the Invention

This invention relates to a method for recovering solid molybdenum compounds. More particularly, this invention relates to a method for recovering solid molybdenum compounds from a hydrocarbon fraction having hydrocarbon soluble molybdenum compounds dissolved therein. Still more particularly, this invention relates to a method for the recovery of solid molybdenum compounds from a heavy liquid hydrocarbon fraction containing contaminating quantities of hydrocarbon soluble molybdenum compounds.

In its more particular aspects, this invention relates to an improvement in a process for the epoxidation of an olefin with an organic hydroperoxide in the presence of a soluble molybdenum peroxidation catalyst wherein the reaction mixture is resolved into fractions, including a substantially anhydrous heavy liquid fraction containing soluble molybdenum epoxidation catalyst and from which the solubilized molybdenum catalyst is precipitated by treating the heavy fraction with an aqueous solution of a molar excess of sodium borate relative to the gram atoms of molybdenum in the heavy fraction. The precipitated molybdenum can be separated from the heavy fraction by filtration in order to provide a filtrate containing less than 100 parts per million of molybdenum which can be safety incinerated without excessive fouling caused by plating out in the incinerator. Further, the 100 ppm or less limit on the molybdenum concentration in the filtrate tends to keep the corrosiveness of the molybdenum solution at acceptable levels. The molybdenum trioxide liberated by the burning of a filtrate containing 100 ppm molybdenum or less can be recovered by conventional bag filters or similar devices.

2. Prior Art

A process for the manufacture of substituted epoxides from alpha olefins such as propylene is disclosed in Kollar U.S. Pat. No. 3,351,653 which teaches that an organic hydroperoxide such as tertiary butyl hydroperoxide can be reacted with the olefin in the presence of a molybdenum catalyst. When the olefin is propylene and the hydroperoxide is tertiary butyl hydroperoxide, the principal reaction products are propylene oxide and tertiary alcohol. Kollar U.S. Pat. No. 3,351,653 is illustrative of the many patents that have issued relating to the reaction of hydroperoxides with olefins in the presence of molybdenum catalysts. Other references include, for example, U.S. Pat. No. 3,526,645, Wulff et al. U.S. Pat. No. 3,634,464, Harrod et al. U.S. Pat. No. 3,654,317, Sorgenti U.S. Pat. No. 3,666,777, Stein et al. U.S. Pat. No. 3,849,451, etc.

The molybdenum compound that is used to catalyze the epoxidation reaction should be a molybdenum compound that is soluble in the reaction medium. A wide variety of molybdenum compounds have been proposed for this purpose, including the molybdenum compounds disclosed in Kollar U.S. Pat. No. 3,351,653. Thus, U.S. Pat. No. 4,434,975 discloses molybdenum catalysts prepared from saturated alcohols or glycols. See also Cavitt U.S. Pat. Nos. 3,784,482 and 3,787,329.

Sorgenti U.S. Pat. No. 3,573,226 discloses a molybdenum-containing epoxidation catalyst solution prepared by heating molybdenum powder with a stream of unreacted tertiary butyl hydroperoxide in polyhydric compounds and Lines et al. U.S. Pat. No. 3,953,362 discloses molybdenum epoxidation catalysts prepared by reacting an oxygen-containing molybdenum compound with hydrogen peroxide and an amine.

The reaction product that is formed will contain not only unreacted organic hydroperoxide and unreacted olefin, the desired epoxide reaction product and the alcohol corresponding to the hydroperoxide feedstock, but will also contain impurities formed during the course of the reaction or introduced into the reaction mixture with the feed components. Among the impurities that are present are acidic oxygen-containing contaminants and by-products including acetone, formic acid, acetic acid, isobutyric acid, the methyl esters of such acids, etc.

After the desired reaction products have been recovered from the reaction mixture, the remaining components of the reaction mixture must be processed for recycle or disposal. The processing of the remaining components presents a problem insofar as the molybdenum catalyst is concerned, because it will normally be present in the reaction mixture in a very small amount, usually less than 1000 ppm.

Normally, after the separation of the desired reaction products the molybdenum will be present in a heavy organic stream which may be a distillate bottoms fraction that remains after unreacted propylene, propylene oxide and olefin oxide epoxide and product alcohol have been recovered.

Levine U.S. Pat. No. 3,819,663 discloses a method for recovering the molybdenum from the heavy organic stream by evaporating most of the liquid components from the stream in a wiped film evaporator in order to provide a residue which Levine states can be recycled back to the reaction mixture.

Such concentration usually leads to a concentration of acids and polyglycols and the presence of these materials in the recycle catalyst solution leads to lower epoxide selectivities and, therefore, it is often not feasible to recycle the molybdenum to the reaction zone and it must be recovered for disposal (e.g., to a company that reclaims molybdenum from solids).

U.S. Pat. No. 3,463,604 discloses the use of ammonium phosphate and related compounds to precipitate molybdenum.

U.S. Pat. No. 3,887,361 discloses heating the effluent in the presence of tertiary butyl alcohol to form a solid precipitate.

U.S. Pat. No. 4,317,802 discloses a related process wherein the effluent is heated with water below the saturation point to precipitate aluminum. U.S. Pat. Nos. 4,485,074 and 4,547,345 disclose processes wherein the epoxidation effluent is heated with an inert gas and with water in order to induce precipitation. A related process is disclosed in European patent application No. 56,740.

Another patent, U.S. Pat. No. 4,317,801 discloses the use of aqueous hydrogen sulfide to precipitate the molybdenum.

However, if a molybdenum recovery process is to be satisfactory, the precipitation must be so complete that the heavy fraction from which the molybdenum is removed can be burned, for example, without fouling the incinerator or causing excessive corrosion in the incinerator.

SUMMARY OF THE INVENTION

In general, this invention relates to a method for substantially completely removing soluble molybdenum compounds from a solvent solution in which they are contained by treating the solution with an aqueous solution of sodium meta borate.

In its more specific aspects, this invention relates to an improvement in the process for the epoxidation of an olefin with an organic hydroperoxide in the presence of a soluble molybdenum peroxidation catalyst wherein the reaction mixture is resolved into a plurality of fractions including a substantially anhydrous heavy liquid fraction containing the soluble molybdenum epoxidation catalyst, the improvement of the present invention being a method for removing substantially all of the molybdenum from the heavy liquid fraction by adding a controlled amount of an aqueous solution of sodium meta borate thereto to provide a mixture which is heated under conditions of temperature and pressure sufficient to substantially completely precipitate the soluble molybdenum compound from the heavy fraction.

BACKGROUND OF THE INVENTION

As mentioned above, it is known to react an olefin with an organic hydroperoxide in the presence of a soluble molybdenum catalyst in order to provide an epoxide corresponding to the olefin and an alcohol corresponding to the hydroperoxide. A preferred olefin is propylene and a preferred hydroperoxide is tertiary butyl hydroperoxide, in which case, the products are propylene oxide and tertiary butyl alcohol.

The reaction is catalyzed by a soluble molybdenum catalyst which is ordinarily present in the reaction mixture in a catalytic amount, such as an amount of less than about 100 ppm of reaction mixture.

The reaction mixture will also contain impurities either formed as by-products during the course of the epoxidation reaction or as impurities introduced into the reaction mixture with the feedstocks. The impurities include acidic oxygen-containing compounds such as acetone, formic acid, acetic acid, isobutyric acid and methyl esters of such acids.

As a consequence, the reaction mixture withdrawn from the reaction zone will comprise not only the olefin and organic hydroperoxide feed materials and the corresponding epoxide and alcohol products, but also impurities such as those mentioned above which are formed or introduced into the reaction mixture. The reaction mixture will also contain the solubilized molybdenum catalyst.

The reaction mixture is typically separated by distillation into a plurality of fractions such as an unreacted olefin fraction, an epoxide product fraction, a product alcohol fraction, etc.

Such products are usually recovered from a distillation zone as distillate products so that there is also formed a heavy liquid fraction containing unrecovered components of the reaction mixture, the acidic oxygen contaminants and the dissolved molybdenum catalyst.

If the heavy fraction is to be disposed of as a waste product, the presence of the soluble molybdenum catalyst presents a serious problem, because of the danger of pollution to either the air or ground. However, to the extent that the molybdenum can be recovered as a solid product, it does not present a pollution product because it can be sold to a company that specializes in the recovery of metals from solid products.

Even then, however, there may be a problem if any of the streams are to be disposed of by burning because residual quantities of molybdenum remaining in the heavy fraction can result in fouling and corrosion of the incinerator. In general, it is considered necessary if the heavy fraction is to be burned that it contain not more than about 100 ppm of molybdenum and, preferably, significantly less to prevent fouling and corrosion of the incinerator. The molybdenum trioxide liberated in such burning could be collected by using bag filters or other similar devices.

In accordance with the present invention, the heavy fraction is treated in a manner such that substantially all of the molybdenum is removed therefrom by precipitation to thereby provide a liquid fraction that can be safely burned and a solid product fraction containing substantially all of the molybdenum.

In accordance with the present invention, an aqueous solution is prepared containing from about 1 to about 10 wt. % of sodium meta borate, and more preferably, from about 2 to about 4 wt. % of sodium meta borate.

The aqueous solution of sodium meta borate is added to the heavy fraction in an amount, based on the weight of the heavy fraction, within the range of about 1 to about 10 wt. %, and more preferably from about 2.5 to about 7.5 wt. %, such that a 50–100% molar excess of sodium meta borate is present in the mixture on the basis of the gram atoms of molybdenum originally present in the heavy fraction. Suitably, from about 1.5 to 2.0 moles of sodium meta borate will be present, per gram atom of molybdenum in the heavy fraction.

The mixture is maintained under precipitation conditions including a temperature ranging from ambient temperature up to about 100° C. and a pressure ranging from about 0 to about 1000 psig. for about 0.5 to 5 hours sufficient to precipitate about 95 wt. % or more of the soluble molybdenum originally present in the heavy fraction.

The resultant mixture is filtered to separate the precipitate and to provide a filtrate which suitably contains not more than about 100 ppm of molybdenum. It will be understood that the mole ratio of sodium meta borate to gram atoms of molybdenum and the weight percent of water in respect of the weight of the heavy fraction will be adjusted such that a minimum amount of molybdenum will remain in the filtrate, such as a concentration as low as about 30 ppm.

In its more specific aspects, in accordance with the present invention, propylene is added to a tertiary butyl alcohol solution of tertiary butyl hydroperoxide containing not more than about 1000 ppm of a dissolved molybdenum catalyst to react the propylene with the tertiary butyl hydroperoxide to thereby provide propylene oxide and additional tertiary butyl alcohol as the principal reaction products. As a consequence, the reaction mixture that is formed will be composed principally of unreacted propylene, unreacted tertiary butyl hydroperoxide, propylene oxide and tertiary butyl alcohol. Also present in the reaction mixture will be the solubilized molybdenum catalyst and reaction by-products such as, for example, a minor amount of ditertiary butyl peroxide and acidic oxygen-containing impurities and by-products including acetone, formic acid, acetic acid, isobutyric acid and methyl esters of such acids.

The reaction mixture is withdrawn from the reaction zone and separated by any suitable means such as, for example, by distillation in a distillation zone into a plurality of fractions including a distillate recycle propylene fraction, a distillate propylene oxide product fraction and a distillate tertiary butyl alcohol product fraction. As a consequence, there will remain a heavy liquid fraction, typically a distillation bottoms fraction comprising unrecovered components of the reaction mixture, principally unrecovered tertiary butyl alcohol, unrecovered tertiary butyl hydroperoxide, the acidic oxygen-containing contaminants and the solubilized molybdenum catalyst, which will normally be present in an amount constituting less than 1000 ppm of the heavy fraction, and typically, from about 500 to 800 ppm.

In accordance with the present invention, an aqueous solution of sodium meta borate is prepared containing from about 1 to 10 wt. % of sodium meta borate and preferably from about 2 to 4 wt. %. From about 2.5 to 7.5 wt. % of the aqueous solution of sodium meta borate is added to the heavy fraction, based on the weight of the heavy fraction to thereby provide an aqueous mixture which will be held in the precipitation zone under conditions of temperature and pressure for a time sufficient to precipitate the molybdenum from the heavy fraction. Suitably, the precipitation conditions will include a temperature ranging from about ambient temperature to about 100° C., a pressure from about 0 to about 1000 psig., and a holding time of about 0.5 to 5 hours. Preferably, the aqueous mixture is maintained at atmospheric pressure and temperatures of 75°–90° C. for about 0.75 to 1.5 hours whereby molybdenum will be precipitated from the heavy fraction to form a precipitation mixture which is then separated by any suitable means such as centrifugation, filtration, decantation, evaporation, etc., and preferably by filtration, to provide a solid product containing substantially all of the molybdenum and a filtrate or liquid product containing a reduced amount of molybdenum, such as 100 ppm of molybdenum or less.

By adjusting the ratios of the sodium meta borate and water to the molybdenum and the heavy fraction, and by adjusting the precipitation conditions, it is possible to provide filtrates containing minimal (<100 ppm) amounts of dissolved molybdenum. The process of the present invention can provide a liquid filtrate fraction containing as little as 30 ppm of dissolved molybdenum. However, if the filtrate is to be burned, it should contain not more than about 100 ppm of dissolved molybdenum. In general, the precipitation conditions should be regulated so as to cause the precipitation of about 95 wt. % or more of the dissolved molybdenum originally present in the heavy fraction.

WORKING EXAMPLES

The invention will be illustrated by the following working examples which are given by way of illustration only.

An epoxidation catalyst bottoms stream obtained by stripping propylene, propylene oxide and low boiling impurities including TBA from an epoxidation reactor effluent stream was composed primarily of TBA, contained 9.48% TBHP, and had an acid number of 14.10 mg KOH/g sample, and contained 677 ppm molybdenum. The epoxidation reactor effluent stream was a stream emerging from an epoxidation reaction zone in which propylene has been reacted with tertiary butyl hydroperoxide solution in TBA in the presence of a soluble molybdenum ethylene glycol catalyst.

EXAMPLE 4

(Table I) 6195-38

Treatment of 200.0 g of epoxidation catalyst bottoms (5815-73-1) with 0.583 grams of a 50% aqueous solution of sodium metaborate and 10.0 grams of added water at 75° C. with stirring for 1.0 hour resulted in a cloudy mixture with solids present. After cooling, the reaction mixture was filtered with the filtrate weighing 206.3 g. The filtrate was analyzed for TBHP (8.76%), acid number (12.32 mg KOH/g sample), pH (5.1), and 27 ppm of molybdenum (moly). A molybdenum balance, [(g moly out/g moly in)×100], indicates that only 4.11% of the molybdenum originally present in the feed remained in the filtrate.

EXAMPLES 7 AND 10

(Table I) 6195-49 and 6195-51

These examples are essentially similar to Example 4 (6195-38) above, except more sodium metaborate used. The molybdenum that remained in the filtrates was still about 4–5% basis the molybdenum in the feed. The use of "extra" sodium metaborate over a 50% excess (mole % excess basis g atoms of molybdenum present) does not lead to further molybdenum removal.

EXAMPLES 3, 6, 9

(Table I) 6195-37, -48, -50

These examples employ similar amounts of sodium meta borate relative to molybdenum, but a lesser amount of added water (1.6–1.8%) and the molybdenum precipitation is less complete, with 9–22% remaining in the filtrate.

EXAMPLE 2, 5, 8, 1

(Table I) 6195-36, -33, -34 and -35

These examples employ the least amount of added water (0–0.3%) and the molybdenum remaining in the filtrate amounted to 90–93% of that feed.

EXAMPLES 11-17

(NB 6195-7, 8, 9, 11, 13, 14 and 15)

These examples involved treatment of epoxidation catalyst bottoms with water in increasing amounts (1%, 2%, 3%, 4%, 5%, 7.5% and 10% basis total treatment charge of epoxidation catalyst bottoms plus water). The water-epoxidation catalyst bottoms mixture was stirred for one hour at 83°–87° C. and cooled. Only in the runs with 7.5 and 10% added water was filtration needed. In no cases did two layers form. In all runs the filtrate or product contained essentially the same amount of molybdenum as charged. In other words, the water at various levels (below and above those in Examples 1–10) alone (without the sodium meta borate) will not precipitate molybdenum from epoxidation catalyst bottoms using the reaction conditions of about 75°–90° C. and 1.0 hour reaction time. Therefore, the precipitations described in Examples 2–10, and especially in Examples 4, 7 and 10, where the molybdenum precipitation was greater than 95% of the molybdenum contained in the feed to the precipitation zone, were due to presence of both sodium meta borate and water.

TABLE I-A

TREATMENT OF EPOXIDATION CATALYST BOTTOMS WITH SODIUM META BORATE (SMB, $NABO_2.4H_2O$) TO INDUCE PRECIPITATION OF MOLYBDENUM TREATMENT OF EPOXIDATION CATALYST BTMS WITH SODIUM META BORATE ($NABO_2.4H_2O$, SMB) TO INDUCE PPTN OF MOLYBDENUM

| Ex. | NB Run # | ETM NB # | Grams Fed | Wt. % TBHP | ppm Moly | Acid # Mg KOH | Grams TBHP Fed | Grams MO Fed | G Atom MO Fed | Moles Acid Fed | Grams Formate Fed | Grams Acetate Fed | Grams Isobutyrate Fed |
|---|---|---|---|---|---|---|---|---|---|---|---|---|---|
| 1 | 6195-36 | 5815-73-1 | 200.0 | 9.48 | 677 | 14.10 | 18.96 | 0.1354 | .001410 | .05027 | 1.24 | 0.78 | 0.28 |
| 2 | 6195-33 | 5815-73-1 | 200.0 | 9.48 | 677 | 14.10 | 18.96 | 0.1354 | .001410 | .05027 | 1.24 | 0.78 | 0.28 |
| 3 | 6195-37 | 5815-73-1 | 200.0 | 9.48 | 677 | 14.10 | 18.96 | 0.1354 | .001410 | .05027 | 1.24 | 0.78 | 0.28 |
| 4 | 6195-38 | 5815-73-1 | 200.0 | 9.48 | 677 | 14.10 | 18.96 | 0.1354 | .001410 | .05027 | 1.24 | 0.78 | 0.28 |
| 5 | 6195-34 | 5815-73-1 | 200.0 | 9.48 | 677 | 14.10 | 18.96 | 0.1354 | .001410 | .05027 | 1.24 | 0.78 | 0.28 |
| 6 | 6195-48 | 5815-73-1 | 200.0 | 9.48 | 677 | 14.10 | 18.96 | 0.1354 | .001410 | .05027 | 1.24 | 0.78 | 0.28 |
| 7 | 6195-49 | 5815-73-1 | 200.0 | 9.48 | 677 | 14.10 | 18.96 | 0.1354 | .001410 | .050267 | 1.24 | 0.78 | 0.25 |
| 8 | 6195-35 | 5815-73-1 | 200.0 | 9.48 | 677 | 14.10 | 18.96 | 0.1354 | .001410 | .05027 | 1.24 | 0.78 | 0.28 |
| 9 | 6195-50 | 5815-73-1 | 200.0 | 9.48 | 677 | 14.10 | 18.96 | 0.1354 | .001410 | .05027 | 1.24 | 0.78 | 0.28 |
| 10 | 6195-51 | 5815-73-1 | 200.0 | 9.48 | 677 | 14.10 | 18.96 | 0.1354 | .001410 | .05027 | 1.24 | 0.78 | 0.28 |

TABLE I-B

TREATMENT OF EPOXIDATION CATALYST BOTTOMS WITH SODIUM META BORATE (SMB, $NABO_2.4H_2O$) TO INDUCE PRECIPITATION OF MOLYBDENUM TREATMENT OF EPOXIDATION CATALYST BTMS WITH SODIUM META BORATE ($NABO_2.4H_2O$, SMB) TO INDUCE PPTN OF MOLYBDENUM

| Ex. | SMB Added to PPT Moly * 50% Aq. Soln. SMB Grams | SMB Added to PPT Moly * 50% Aq. Soln. SMB Moles | Water Used to PPT Moly Grams | Reaction Conditions Used for Moly PPTN Experiment Time, Hrs. | Reaction Conditions Used for Moly PPTN Experiment Temp., °C. | Filtrate Grams | Filtrate % of Total Liq. Fed | TBHP Bal. Grams TBHP in Filtrate | Grams Moly in Filtrate | Moly in Filtrate % of Total Moly Fed |
|---|---|---|---|---|---|---|---|---|---|---|
| 1 | 0.292 | .00212 | None | 1.0 | 75° C. | 195.7 | 97.85 | 17.91 | 0.1256 | 92.8 |
| 2 | 0.292 | .00212 | .292 | 1.0 | 75° C. | 199.6 | 99.80 | 18.92 | 0.1263 | 93.3 |
| 3 | 0.292 | .00212 | 3.292 | 1.0 | 75° C. | 193.4 | 97.59 | 17.86 | 0.0298 | 22.0 |
| 4 | 0.292 | .00212 | 10.292 | 1.0 | 75° C. | 206.3 | 98.10 | 18.07 | 0.0056 | 4.1 |
| 5 | 0.389 | .00282 | .389 | 1.0 | 75° C. | 196.9 | 98.26 | 18.08 | 0.1223 | 90.3 |
| 6 | 0.389 | .00282 | 3.389 | 1.0 | 75° C. | 198.2 | 97.45 | 18.41 | 0.0218 | 16.1 |
| 7 | 0.389 | .00282 | 10.389 | 1.0 | 75° C. | 204.9 | 97.39 | 18.56 | 0.0066 | 4.8 |
| 8 | 0.583 | .00423 | .583 | 1.0 | 75° C. | 197.1 | 98.26 | 17.88 | 0.1254 | 92.6 |
| 9 | 0.583 | .00423 | 3.583 | 1.0 | 75° C. | 198.1 | 97.31 | 18.62 | 0.0119 | 8.8 |
| 10 | 0.583 | .00423 | 10.583 | 1.0 | 75° C. | 206.3 | 97.97 | 18.30 | 0.0056 | 4.1 |

TABLE I-C

TREATMENT OF EPOXIDATION CATALYST BOTTOMS WITH SODIUM META BORATE (SMB, $NABO_2.4H_2O$) TO INDUCE PRECIPITATION OF MOLYBDENUM TREATMENT OF EPOXIDATION CATALYST BTMS WITH SODIUM META BORATE ($NABO_2.4H_2O$, SMB) TO INDUCE PPTN OF MOLYBDENUM

| Ex. | Moles Acid in Filtrate | Acid in Filtrate % of Acid Fed | Grams Formate in Filtrate | Formate in Filtrate % of Total Formate Fed | Grams Acetate in Filtrate | Acetate in Filtrate % of Total Acetate Fed | Isobutyrate in Filtrate % of Total Isobuty Fed | Grams Isobutyrate in Filtrate | pH of Solution Filtered |
|---|---|---|---|---|---|---|---|---|---|
| 1 | 0.04863 | 96.7 | 1.10 | 88.4 | 0.61 | 77.8 | 28.0 | 0.078 | 4.1 |
| 2 | 0.04821 | 95.9 | 1.16 | 93.4 | 0.66 | 84.4 | 42.8 | 0.120 | 3.5 |
| 3 | 0.04636 | 92.2 | 1.21 | 97.4 | 0.71 | 91.6 | 42.5 | 0.119 | 4.2 |
| 4 | 0.04531 | 90.1 | 1.05 | 34.8 | 0.45 | 58.2 | 29.5 | 0.082 | 5.1 |
| 5 | 0.04819 | 95.9 | 0.87 | 69.9 | 0.30 | 37.9 | 35.2 | 0.098 | 4.0 |
| 6 | 0.05335 | 106.1 | 1.09 | 87.9 | 0.81 | 104.2 | 134.5 | 0.377 | 4.5 |
| 7 | 0.05259 | 104.6 | 1.00 | 80.6 | 0.82 | 105.1 | 80.5 | 0.225 | 5.2 |
| 8 | 0.04740 | 94.3 | 1.16 | 93.8 | 0.75 | 96.0 | 63.4 | 0.177 | 4.0 |
| 9 | 0.05332 | 106.1 | 0.99 | 80.0 | 0.77 | 98.7 | 63.7 | 0.178 | 5.1 |
| 10 | 0.04817 | 95.8 | 0.95 | 76.5 | 0.74 | 95.2 | 51.6 | 0.144 | 5.2 |

Turning now to Tables I-A, I-B and I-C, and first to Examples 1–4, it will be observed that when about 2 mole equivalents of sodium meta borate per gram atom of molybdenum in the feed were used in Example 1 without any water, substantially all of the dissolved molybdenum remained in the filtrate. A substantially equivalent result was obtained in Example 2 when the amount of water used was the molar equivalent of the amount of sodium meta borate employed, namely, 0.292 grams. In Example 3, however, when in excess of 3 grams of water were used, about 78% of the molybdenum precipitated such that the filtrate contained only 22 wt. % of the dissolved aluminum originally present in the feedstock. This constitutes the use of about 1.6 wt. % of water on the basis of the weight of the heavy fraction. When about 5 wt. % of water was added, at the same molar ratio of sodium meta borate to dissolved aluminum in Example 4, 95.3 wt. % of the molybdenum was filtered and the filtrate contained only 4.1 wt. % of the molybdenum originally present in the filtrate or about 30 ppm.

Next, turning to Examples 5-7, it will be observed from Example 5 that when about 0.15 wt. % of water was present, unsatisfactory results were obtained even though the aqueous solution contained about 2.9 moles of sodium meta borate per gram atom of molybdenum. Adverse results were obtained in Example 6 using the same amount of sodium meta borate and about 1.6 wt. % of water. In this case, about 84% of the dissolved molybdenum was precipitated so that the filtrate contained only 16.1 wt. % of the dissolved molybdenum originally present in the feedstock.

In Example 7, however, wherein about 5 wt. % of the aqueous solution was used, with a 2/1 molar ratio of sodium meta borate to dissolved molybdenum, the filtrate contained about 4.8 wt. % of the dissolved molybdenum originally in the feed or, roughly, about 30 ppm of dissolved molybdenum in the filtrate.

Finally, in Examples 8-10 it is seen that the same pattern repeats itself, adverse results being obtained when the amount of water added to the heavy fraction was only about 0.16 wt. % even though about 4.3 moles of sodium borate per gram atom of molybdenum were present.

In Example 9, when the water content was increased to about 1.8 wt. % of the weight of the charge, over 90% of the molybdenum was precipitated, leaving only about 8.8 wt. % of the dissolved molybdenum in the filtrate in comparison with the amount of dissolved molybdenum in the feedstock.

However, increasing the water content to about 5.3 wt. %, on the basis of the weight of the charge stock, with the same molar ratio of sodium metal borate to gram atoms of molybdenum did not result in an improvement over the results obtained in Example 4.

It is seen from the foregoing that the use of anhydrous or aqueous sodium meta borate in the amount of about 0.14 to about 0.29 wt. % of water, on the basis of the charge together with a 50, 100 and 200 molar percent excess of sodium meta borate relative to the gram atoms of molybdenum did not produce a satisfactory molybdenum precipitation. However, the use of about 4.8 to about 5 wt. % of added water along with a 50, 100 and 200 mole percent excess of sodium meta borate relative to the gram atoms of molybdenum afforded substantially complete precipitation of the molybdenum.

Having thus described our invention, what is claimed is:

1. A process for substantially completely removing molybdenum dissolved in a substantially anhydrous organic solution which comprises the steps of:
    preparing an aqueous solution of sodium meta borate containing from about 1 to about 10 wt. % of dissolved sodium meta borate,
    adding to said organic solution from about 1 to about 10 wt. % of said aqueous solution of sodium meta borate, based on the weight of said organic solution, in an amount sufficient to provide a molar excess of sodium meta borate, based on the gram atoms of dissolved molybdenum in said organic solution, to provide a mixture,
    maintaining said mixture at a temperature of ranging from about ambient temperature up to about 100° C. at a pressure of about 0 to about 1,000 psig for about 0.5 to about 5 hours, sufficient to precipitate at least about 95 mol % of said soluble molybdenum from said mixture, and
    filtering said mixture to provide a filtrate containing less than about 100 ppm of molybdenum.

2. A method as in claim 1 wherein said organic solution has from 500 to about 1,000 ppm of molybdenum dissolved therein and wherein said filtrate contains not more than about 100 ppm of dissolved molybdenum.

3. A method as in claim 2 wherein from about 5 to about 10 wt. % of said aqueous solution is added to said organic solution, based on the weight of said organic solution, the amount of said aqueous solution added to said organic solution being sufficient to provide a molar excess of up to about 200 mol % of said sodium meta borate, based on the gram atoms of molybdenum originally dissolved in said organic solution.

4. A method as in claim 3 wherein said mixture is maintained at a temperature of about 50° to about 100° C., for about ¾ to about 1.5 hours.

5. In a process for the epoxidation of an olefin with an organic hydroperoxide in the presence of a soluble molybdenum peroxidation catalyst, wherein the reaction mixture is resolved into fractions including a substantially anhydrous heavy liquid fraction containing the soluble molybdenum epoxidation catalyst, the improvement for substantially completely removing said solubilized molybdenum from said heavy fraction which comprises the steps of:
    preparing about a 1 to about 10 wt. % aqueous solution of sodium meta borate,
    adding from about 1 to about 10 wt. % of said aqueous solution to said heavy fraction, based on the weight of said portion of said heavy fraction to provide a mixture, in an amount sufficient to provide a molar excess of sodium meta borate, based on the gram atoms of dissolved molybdenum in said heavy fraction, to provide a mixture,
    maintaining said mixture at a temperature of ranging from about ambient temperature up to about 100° C. at a pressure of about 0 to about 1,000 psig for about 0.5 to about 5 hours, sufficient to precipitate at least about 95 mol % of said soluble molybdenum from said heavy fraction, and
    filtering said heavy fraction to provide a filtrate containing not more than about 100 ppm of molybdenum.

6. A method as in claim 5 wherein said heavy fraction has from 500 to about 1,000 ppm of molybdenum dissolved therein.

7. A method as in claim 6 wherein said aqueous solution contains a molar excess of up to about 200 mol % of said sodium borate, based on the gram atoms of molybdenum in said heavy fraction and wherein from about 5 to about 10 wt. % of said aqueous solution is added to said heavy fraction, based on the weight of said fraction.

8. A method as in claim 7 wherein said mixture is maintained at a temperature of about 50° to about 100° C., for about ¾ to about 1.5 hours.

9. In a process for the preparation of propylene oxide wherein propylene is reacted with a tertiary butyl hydroperoxide in solution in tertiary butyl alcohol in the presence of a soluble molybdenum catalyst under peroxidation reaction conditions to provide a reaction mixture comprising unreacted propylene, propylene oxide, tertiary butyl alcohol, unreacted tertiary butyl hydroperoxide, acidic oxygen-containing by-products including acetone, formic acid, acetic acid, isobutyric acid, and methyl esters of said acids, and said molybdenum catalyst and wherein said reaction mixture is resolved by distillation into product fractions including a substantially anhydrous heavy liquid fraction containing tertiary butyl hydroperoxide, tertiary butyl alcohol, said oxygen-containing impurities and substantially all of the soluble molybdenum epoxidation catalyst originally present in said reaction mixture, the improvement for substantially completely removing solubilized molybdenum from said heavy fraction which comprises the steps of:

preparing about a 1 to about a 10 wt. % aqueous solution of sodium meta borate, adding from about 1 to about 10 wt. % of said aqueous solution to said heavy fraction, based on the weight of said portion of said heavy fraction to provide a mixture, in an amount sufficient to provide a molar excess of sodium meta borate, based on the gram atoms of dissolved molybdenum in said heavy fraction, to provide a mixture, maintaining said mixture at a temperature of ranging from about ambient temperature up to about 100° C. at a pressure of about 0 to about 1,000 psig for about 0.5 to about 5 hours, sufficient to precipitate at least about 95 mol % of said soluble molybdenum from said heavy fraction, and filtering said heavy fraction to provide a filtrate containing substantially all of said acidic oxygen-containing impurities but not more than about 100 ppm of soluble molybdenum.

10. A method as in claim 9 wherein said heavy fraction has from 500 to about 1,000 ppm of molybdenum dissolved therein.

11. A method as in claim 10 wherein said aqueous solution contains a molar excess of up to about 200 mol % of said sodium meta borate, based on the gram atoms of molybdenum in said heavy fraction and wherein from about 5 to about 10 wt. % of said aqueous solution is added to said heavy fraction, based on the weight of said fraction.

12. A method as in claim 11 wherein said mixture is maintained at a temperature of about 50° to about 100° C., for about ¾ to about 1.5 hours.

* * * * *